(12) United States Patent
Pickens

(10) Patent No.: US 11,037,675 B1
(45) Date of Patent: Jun. 15, 2021

(54) SCREENING-BASED AVAILABILITY OF COMMUNICATIONS DEVICE FEATURES

(71) Applicant: Securus Technologies, Inc., Carrollton, TX (US)

(72) Inventor: Connor Pickens, Little Elm, TX (US)

(73) Assignee: Securas Technologies, LLC, Carrollton, TX (US)

( * ) Notice: Subject to any disclaimer, the term of this patent is extended or adjusted under 35 U.S.C. 154(b) by 205 days.

(21) Appl. No.: 15/911,242

(22) Filed: Mar. 5, 2018

(51) Int. Cl.
*G16H 40/20* (2018.01)
*G16H 20/70* (2018.01)
*G16H 50/30* (2018.01)
*G06F 21/62* (2013.01)

(52) U.S. Cl.
CPC ............. *G16H 40/20* (2018.01); *G16H 20/70* (2018.01); *G16H 50/30* (2018.01)

(58) Field of Classification Search
CPC ... G06F 1/00–2221/2153; G16H 10/00–80/00; H04M 1/00–2250/74
See application file for complete search history.

(56) References Cited

U.S. PATENT DOCUMENTS

| | | | |
|---|---|---|---|
| 8,814,359 B1 * | 8/2014 | Pompilio, III | G06F 9/453 351/223 |
| 9,160,866 B1 * | 10/2015 | Keiser | H04M 15/8083 |
| 9,380,082 B1 * | 6/2016 | Keiser | H04N 7/181 |
| 9,659,477 B1 * | 5/2017 | Obaidi | G06F 1/163 |
| 9,723,040 B1 * | 8/2017 | Lubbehusen | H04L 43/10 |
| 9,965,746 B1 * | 5/2018 | Keiser | G06Q 10/109 |
| 10,050,668 B1 * | 8/2018 | Keiser | H04B 3/54 |
| 2007/0112948 A1 * | 5/2007 | Uhlik | H04L 12/1403 709/223 |

(Continued)

FOREIGN PATENT DOCUMENTS

WO  WO-2015157108 A1 * 10/2015 ........... G06F 9/4893

OTHER PUBLICATIONS

Jewkes et al., "A Brave New World: the problems and opportunities presented by new media technologies in prisons," Criminology and Criminal Justice, vol. 16, Issue 5. (Year: 2016).*

*Primary Examiner* — Elaine Gort
*Assistant Examiner* — Jonathon A. Szumny
(74) *Attorney, Agent, or Firm* — Fogarty LLP

(57) ABSTRACT

System, devices and methods are provided for providing a resident of a controlled-environment facility with services via a communications device, where access to software components, software features and/or content on the communication device may be restricted based on the results of a mental health assessment administered via the communication device. The communication device utilized by the resident connects to a resident communications system that provides use of requested software elements. If a requested software element is determined to be restricted, the resident must complete a mental health assessment that determines a distress level of the resident. The distress level may be determined based on inputs provided by the resident and sensor inputs collected by the communication device. If the mental health assessment indicates the distress level of the resident is below a threshold, the resident is allowed to utilize the software element.

17 Claims, 3 Drawing Sheets

(56) References Cited

U.S. PATENT DOCUMENTS

| | | | | |
|---|---|---|---|---|
| 2008/0109872 | A1* | 5/2008 | Walker | G06Q 10/00 726/1 |
| 2011/0118555 | A1* | 5/2011 | Dhumne | A61B 5/16 600/300 |
| 2011/0162067 | A1* | 6/2011 | Shuart | G06F 21/31 726/19 |
| 2011/0164878 | A1* | 7/2011 | Ma | H04B 10/1149 398/79 |
| 2014/0105094 | A1* | 4/2014 | Soundararajan | H04W 48/16 370/312 |
| 2016/0051153 | A1* | 2/2016 | Mously | A61B 5/02444 600/324 |
| 2016/0066181 | A1* | 3/2016 | Henry | H04W 12/06 726/5 |
| 2016/0239932 | A1* | 8/2016 | Sidler | H04L 63/302 |
| 2016/0275546 | A1* | 9/2016 | Kitagishi | G06Q 30/0244 |
| 2016/0286365 | A1* | 9/2016 | Matsushima | H04W 4/10 |
| 2017/0006145 | A1* | 1/2017 | Schriefer | H04M 1/2474 |
| 2017/0147934 | A1* | 5/2017 | Hecht | G06N 20/00 |
| 2017/0193787 | A1* | 7/2017 | Devdas | G08B 21/0261 |
| 2017/0270627 | A1* | 9/2017 | Hodge | G06F 16/24578 |
| 2017/0287315 | A1* | 10/2017 | Kaur | H04W 4/90 |
| 2017/0289764 | A1* | 10/2017 | Yang | H04W 4/025 |
| 2018/0040255 | A1* | 2/2018 | Freeman | A61B 5/742 |
| 2018/0242155 | A1* | 8/2018 | Marass | H04W 12/08 |
| 2018/0300555 | A1* | 10/2018 | Hodge | G08B 13/19663 |
| 2018/0349626 | A1* | 12/2018 | Bender | G06N 20/00 |
| 2019/0045329 | A1* | 2/2019 | Natsume | G01S 5/0294 |
| 2019/0350457 | A1* | 11/2019 | Avitan | A61B 5/681 |
| 2020/0084766 | A1* | 3/2020 | Pawlak | H04B 7/2656 |

* cited by examiner

SCREENING-BASED AVAILABILITY OF COMMUNICATIONS DEVICE FEATURES

TECHNICAL FIELD

The following description relates generally to communications devices provided to residents of a controlled-environment facility, and more particularly to controlling the availability of features of communications devices provided to a resident of a controlled-environment facility based on a mental health screening of the resident.

BACKGROUND OF THE INVENTION

It is estimated that over two million individuals are incarcerated in U.S. prisons and jails. In general, inmates that have been convicted of felony offenses serve longer sentences in prisons (e.g., federal or state prisons), whereas inmates that have been convicted of misdemeanors receive shorter sentences that are frequently served in local jails (e.g., county jail). In addition, upon being detained by authorities, an inmate may serve significant periods of time incarcerated in a local jail while awaiting release on bond and, in some cases, while awaiting trial. During all of these periods of incarceration, an inmate may have opportunities to communicate with the outside world.

By allowing inmates to communicate with friends and family while incarcerated, the justice system aims to facilitate their transition back into society upon release. Traditional visitation sessions provided by controlled-environment facilities include telephone calls and in-person visits. More recently, technological advances have allowed controlled-environment facilities to provide other types of monitored visitation sessions, including audio conferences, video conferences, video messages, email, and online chat sessions. Traditionally, visitation sessions have been conducted using phones, terminals, kiosks, or other such devices that are installed in a fixed location, such as within a designated visitation area of the controlled-environment facility. More recently, visitation sessions may be conducted via portable communications devices issued to inmates on a temporary or permanent basis.

In addition to providing increased opportunities for visitations, additional services may be provided to inmates via an issued portable communications device. For instance, a portable communications device may provide residents with educational and entertainment services. Providing such services to a resident of a controlled-environment facility via a portable communications device may result in misuse of these services by the resident. In certain instances, misuse by the resident may result, at least in part, from the resident's mental health condition. For instance, a resident that is distressed may be more likely to behave in an unauthorized manner during a visitation session. Providing residents with a communication device also results in increased opportunities to monitor and evaluate the mental health condition of a resident, thus improving the ability to identify the residents of a controlled-environment facility that are most in need of counseling services or other mental health resources.

BRIEF SUMMARY

In accordance with various embodiments, a communications device provides services to a resident of a controlled-environment facility. The communication device includes a network interface configured to establish a connection with a resident communications system via one or more network access points located within the controlled-environment facility. The communication device further includes a memory device configured to store operating system program instructions. The communication device further includes one or more processors configured to execute the operating system program instructions, causing the communications device to: connect with the resident communications system to provide the resident with use of a first software element; determine whether the first software element is a restricted software element of the communications device; if the first software element is determined to be a restricted software element, require the resident to complete a mental health assessment; administer the mental health assessment of the resident to determine a distress level of the resident; and allow the resident to utilize the first software element, if the mental health assessment of the resident indicates the distress level of the resident is below a threshold.

In certain additional embodiments of the communication device, the first software element comprises a software module providing the resident with one or more services. In certain additional embodiments of the communication device, the first software element comprises a feature of a software module providing the resident with one or more services. In certain additional embodiments of the communication device, the first software module comprises content provided via a software module providing the resident with one or more services. In certain additional embodiments of the communication device, the mental health assessment indicates the resident is distressed based on inputs provided by the resident and sensor inputs collected by the communications device. In certain additional embodiments, the operating system program instructions further causing the communications device to: require the resident to complete a counseling session, if the mental health assessment of the resident indicates that the resident is distressed; and allow the resident to utilize the first software element, if the resident has completed the counseling session.

In various embodiments, a system provides a resident of a controlled-environment facility with communication services. The system includes one or more network access points coupled to a resident communications system. The system further includes a communications device assigned to the resident, wherein the communications device is configured to connect to the resident communications system via the one or more network access points. The resident communications system is configured to: receive a request from the resident for use of a first software element installed on the communications device; determine whether the first software element is a restricted software element of the communications device; if the first software element is determined to be a restricted software element, require the resident to complete a mental health assessment; administer the mental health assessment of the resident to determine a distress level of the resident; and allow the resident to utilize the first software element, if the mental health assessment of the resident indicates the distress level of the resident is below a threshold.

In certain additional embodiments of the system, the first software element comprises a software module providing the resident with one or more services. In certain additional embodiments of the system, the first software element comprises a feature of a software module providing the resident with one or more services. In certain additional embodiments of the system, the first software module comprises content provided via a software module providing the resident with one or more services. In certain additional embodiments of the system, the mental health assessment indicates the resident is distressed based on inputs provided by the resident and sensor inputs collected by the communications device. In certain additional embodiments of the system, the resident communications system is configured to require the resident to complete a counseling session, if the mental health assessment of the resident indicates that the resident is distressed. In certain additional embodiments of the system, the resident communications system is configured to allow the resident to utilize the first software element, if the resident has completed the counseling session.

In various embodiments, a method provides a resident of a controlled-environment facility with communication services via a communications device utilized by the resident. The method includes connecting communications device with a resident communications system of the controlled-environment facility to provide the resident with use of a first software element; determining whether the first software element is a restricted software element of the communications device; if the first software element is determined to be a restricted software element, requiring the resident to complete a mental health assessment; administering the mental health assessment of the resident to determine a distress level of the resident; and allowing the resident to utilize the first software element, if the mental health assessment of the resident indicates the distress level of the resident is below a threshold.

In certain additional embodiments of the method, the first software element comprises a software module providing the resident with one or more services. In certain additional embodiments of the method, the first software element comprises a feature of a software module providing the resident with one or more services. In certain additional embodiments of the method, the first software module comprises content provided via a software module providing the resident with one or more services. In certain additional embodiments of the method, the mental health assessment indicates the resident is distressed based on inputs provided by the resident and sensor inputs collected by the communications device. In certain additional embodiments, the method further includes requiring the resident to complete a counseling session, if the mental health assessment of the resident indicates that the resident is distressed. In certain additional embodiments, the resident to utilize the first software element, if the resident has completed the counseling session.

BRIEF DESCRIPTION OF THE DRAWINGS

Figure 1:
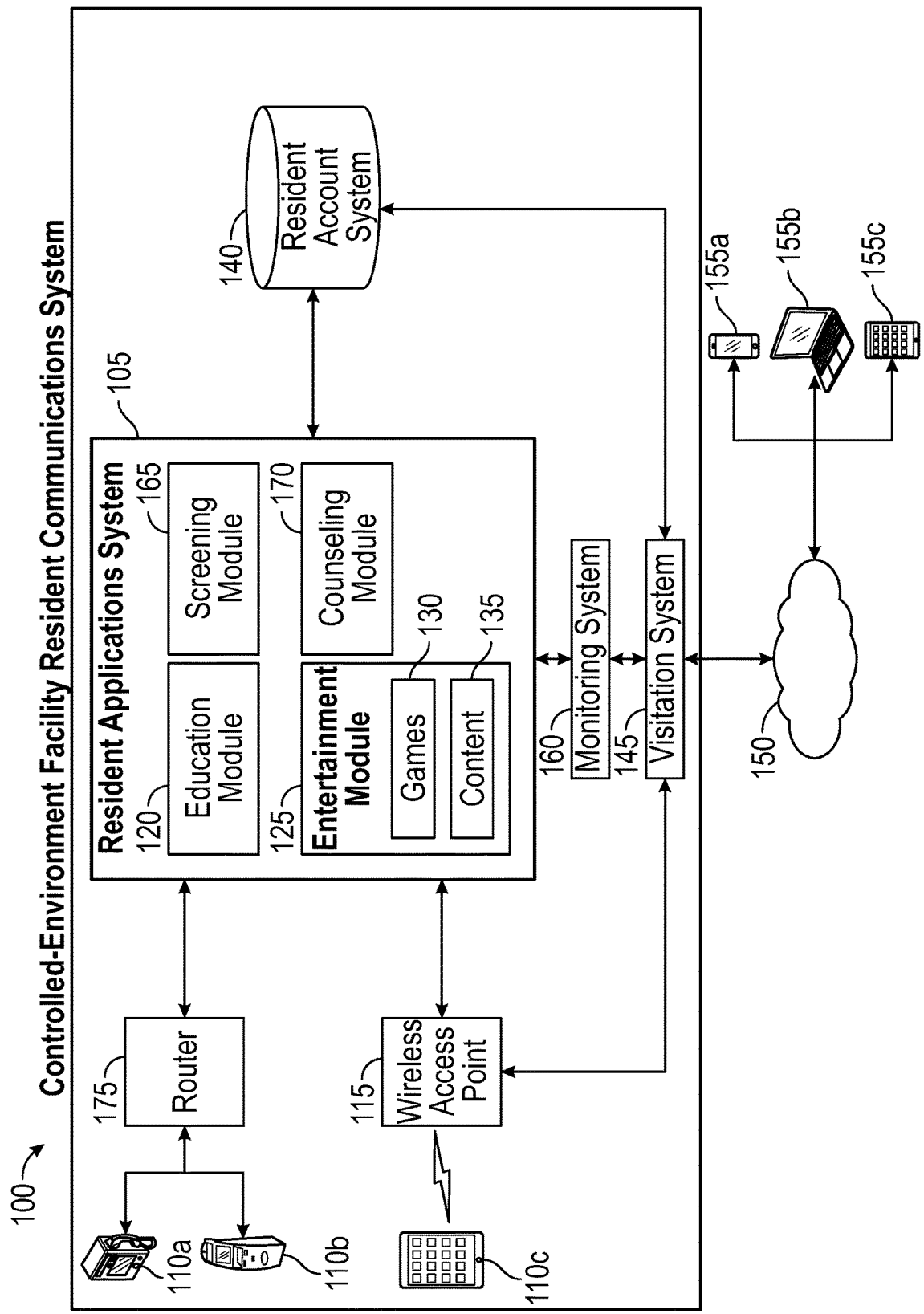

Having thus described the invention in general terms, reference will now be made to the accompanying drawings, which are not necessarily drawn to scale, and wherein:

FIG. 1 is a diagram illustrating certain components of a system according to various embodiments for screening-based availability of features of communications devices provided to residents of a controlled-environment facility.

Figure 2:
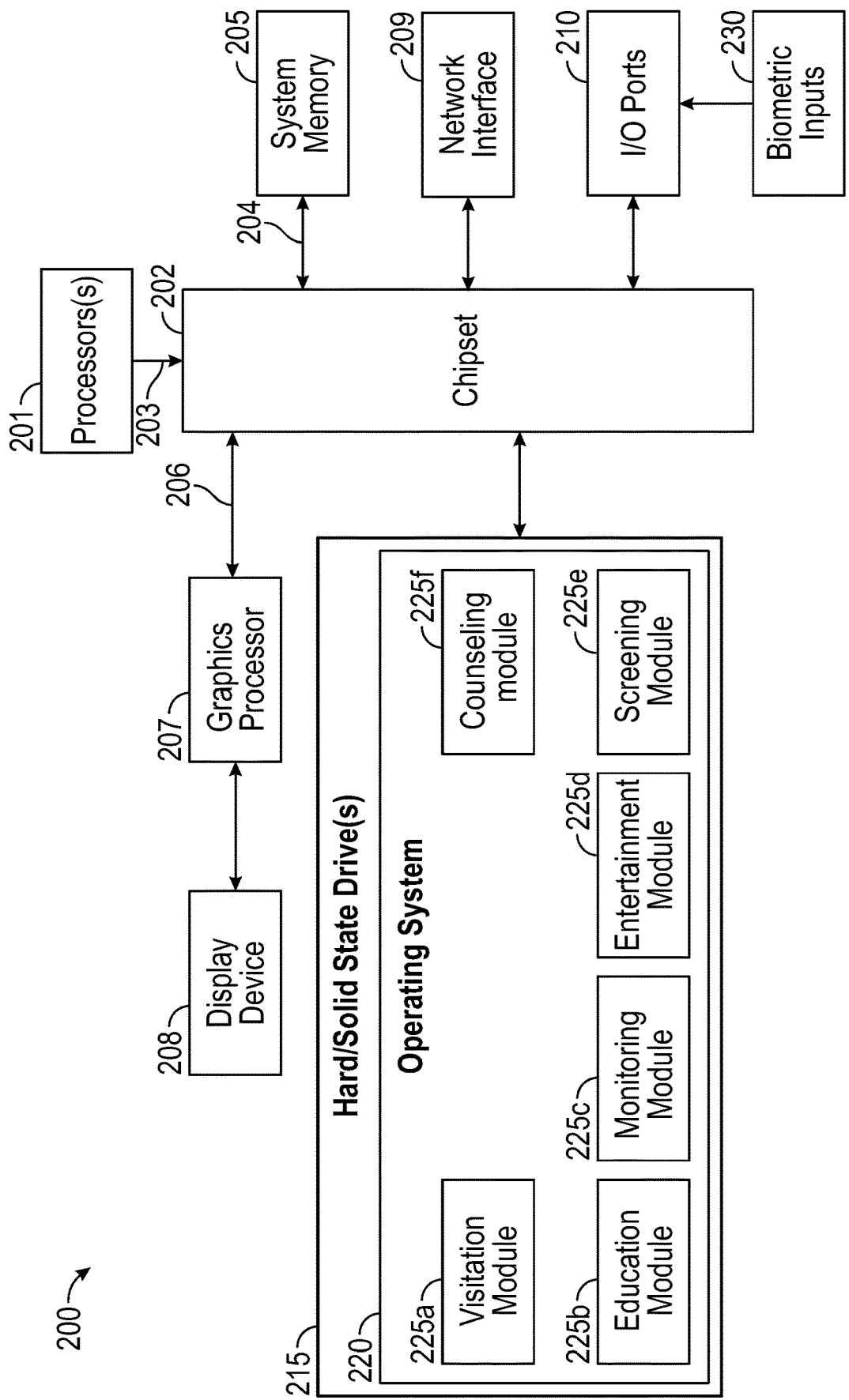

FIG. 2 is a diagram illustrating certain components according to various embodiments of a portable communications device including screening-based availability of device features provided to residents of a controlled-environment facility.

Figure 3:
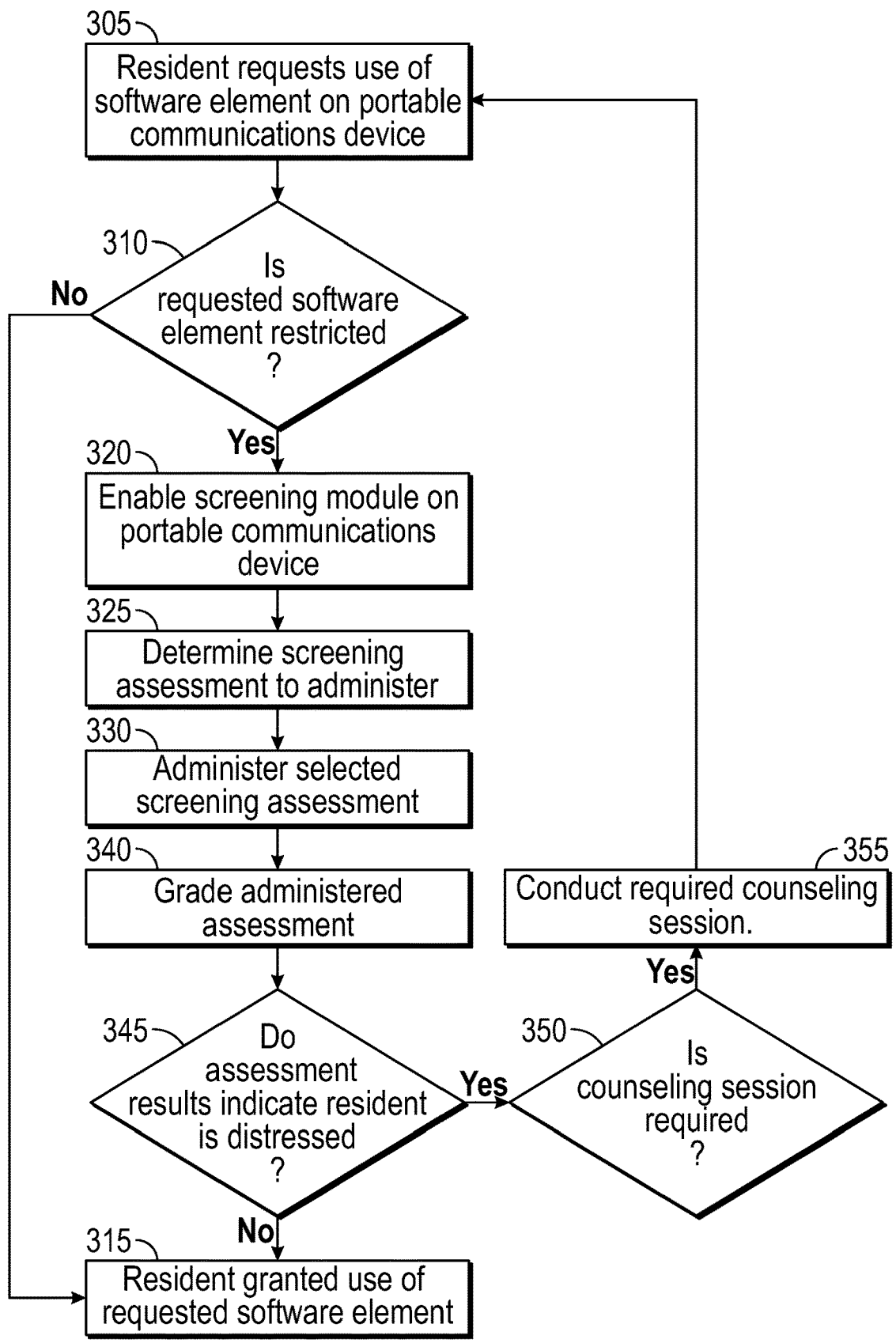

FIG. 3 is a flowchart diagram illustrating certain steps of process according to various embodiments for screening-based availability of features of communications devices provided to residents of a controlled-environment facility.

DETAILED DESCRIPTION

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. One skilled in the art may be able to use the various embodiments of the invention.

For example, embodiments may be implemented within various types of controlled-environment facilities, and persons may be voluntary or involuntary residents of such facilities, whether temporarily or permanently. Examples of controlled-environment facilities may include correctional institutions (e.g., municipal jails, county jails, state prisons, federal prisons, military stockades, juvenile facilities, detention camps, home incarceration environments, etc.), certain healthcare facilities (e.g., certain hospitals and nursing homes, certain mental health facilities, certain rehabilitation facilities, such as drug and alcohol rehabilitation facilities, etc.), certain restricted living quarters (e.g., barracks, certain dormitories, etc.), certain educational facilities, and the like. For convenience of explanation, various examples discussed herein are presented in the context of correctional facilities, or the like. For instance, in some of the embodiments discussed below, a controlled-environment facility may be referred to as a correctional facility, jail or prison, and its residents may be referred to as inmates, arrestees, or detainees. It should be understood, however, that the systems and methods described herein may be similarly applicable to other types of controlled-environment facilities and their respective residents (e.g., a hospital and its patients, a school dormitory and its students, etc.).

FIG. 1 is a diagram illustrating certain components of a resident communications system 100 provided within a controlled-environment facility according to various embodiments. In a controlled-environment facility, the resident communications system 100 may provide residents with a variety of services. In certain instances, the resident may utilize the services provided by the resident communications system 100 via a resident communications device 110*a-c*. In the illustrated embodiment, resident communications system 100 provides residents with visitation session services via a visitation system 145, where the resident may utilize certain of these visitation session services via a supported resident communications devices 110*a-c*, that may include a resident terminal 110*a*, a resident kiosk 110*b* and/or a portable communications device 110*c*. As illustrated, resident communications system 100 also provides residents with a resident applications system 105 that interfaces with the resident communications device 110*a-c* in order to provide various approved software applications to the resident, such as educational, counseling and entertainment software. In various embodiments, resident communications system 100 may provide residents with a variety of additional services via a resident communications device 110*a-c*.

In certain embodiments, resident communications system 100 may be located within a controlled-environment facility, and may be used to provide communications services to residents located at that particular facility. Alternatively, resident communications system 100 may be centrally and/ or remotely located with respect to one or more controlled-environment facilities and be used to provide services to residents at multiple different facilities. Whether local to a particular controlled-environment facility or located remotely, resident communications system 100 may be used to provide communication services to residents of multiple controlled-environment facilities.

One of the services provided to residents by the resident communications system 100 is monitored visitation sessions. In the illustrated embodiment, visitation system 145 allows a resident, using resident communications device 110a-c, to participate in a visitation session with a nonresident participating via a communications device 155a-c that connects to the visitation system 145 via an external network 150, such as the Internet. In various embodiments, the visitation system 145 may provide residents with a selection of different visitation session formats including audio conferences, audio messages, video conferences, video messages, email, online chats and/or text messaging services. In certain instances, the visitation formats available to a resident may depend on factors such as: the capabilities of the resident communications device 110a-c, the resident's designated privilege classification within the controlled-environment facility, and restrictions on types of visitations that are allowed with specific nonresidents. As described with respect to the embodiments of FIGS. 2 and 3, certain restrictions on the use of a resident communications device 110a-c during visitation sessions may be enforced based on the results of mental health screening of the resident.

In the illustrated embodiment, the resident communications system 100 utilizes the resident account system 140 in enforcing security protocols that are applicable to the use of services provided to residents of the controlled-environment facility. For instance, in providing visitation services, the visitation system 145 may determine applicable restrictions based on data stored in the resident account system 140. In certain embodiments, the visitation system 145 may interoperate with the resident account system 140 to limit a resident's visitation sessions to sessions with non-residents whose identities are listed in that resident's Pre-Approved Contact (PAC) and/or Personal-Allowed Number (PAN) list. In some scenarios, the visitation system 145 may also enforce restrictions prohibiting a resident from contacting certain individuals identified in a "do not contact" list. The identity of a non-inmate may be represented on these lists by the phone number of the non-resident, the device presented for use by a non-resident and/or the email addresses or other accounts used by the non-resident. Each resident's PAC, PAN, and/or do not contact list(s) may be stored by the resident account system 140. In certain scenarios, resident account system 140 may also be used to store biometric information used to authenticate individual residents of the controlled-environment facility and/or non-residents that have been authorized for certain visitation system 145 services. In addition to PAC, PAN, and/or do not contact list(s), resident account system 140 may also store other security profiles and rules that are applicable to each resident.

The resident account system 140 may also be used to manage information such as balances in a resident's trust, commissary and/or visitation services accounts. The resident account system 140 may also provide access to other information pertaining to a resident, including for instance a resident's trial schedule, conviction data, criminal record, sentencing data (such as time served, time remaining to be served, and projected release date), counseling history, screening history, cell and cellmate assignments, resident-specific restrictions and warnings, commissary order history, telephone call history, call recordings, known or suspected gang or criminal affiliations, known or suspected affiliates, accomplices, or gang members; and any other information that may be relevant or useful to correctional facility staff to house and maintain residents. In various embodiments, the resident account system 140 may be one or more separate systems, or may be integrated as a component of the resident communications system 100.

Subject to various restrictions and limitations enforced by the visitation system 145, residents may participate in visitation sessions with one or more non-residents 155a-c. Nonresidents may utilize various communications devices in participating in visitation sessions. For instance, a non-resident may participate using a mobile phone 155a, tablet computing device 155c, a personal computer 155b or other communications device capable of interfacing with the visitation system 145. In certain scenarios, a non-resident may participate in a voice visitation session hosted by the visitation system 145 via a traditional telephone via a Publicly Switched Telephone Network (PSTN) interface to the network 150. As described, various other visitation session formats may be supported by visitation system 145. Based on the hardware and software capabilities of the nonresident devices 155a-c, nonresidents may participate in voice, video and/or written (e.g., text, chat, email) visitation sessions.

In the illustrated embodiment, resident communications system 100 includes a monitoring system 160 configured to perform various monitoring operations related to the resident's use of the services provided by the system. In particular, the tools provided by the monitoring system provide the ability to monitor resident's use of software applications provided via the resident applications system 105. The monitoring system 160 also provides various tools for automated and manual monitoring of visitation sessions conducted via the visitation system 145. The monitoring system 160 may include tools that allow staff to monitor live and recorded visitation sessions. The monitoring system 160 may record the visitation sessions conducted via the visitation system 145, such as by generating written transcripts, audio and/or video files of the visitation session. These recorded visitation sessions may be stored to a database maintained by the monitoring system 160. The monitoring system 160 may also provide tools that allow staff to mark and annotate events observed in a recorded visitation session. The monitoring system 160 may also provide tools that allow staff to search recorded visitation sessions in support of investigative activities. Additional monitoring may be provided by the monitoring system 160 via keyword detection, gesture recognition, and other tools intended to detect unauthorized or illicit behavior during a visitation session.

In certain embodiments, resident communications device 110a-c may be a personal wireless device 110c, such as a tablet device or a smartphone device. As described in additional detail with regard to the embodiment of FIG. 2, the portable communications device 110c may include a camera, display, microphone and speakers and may allow the resident to participate in visitation sessions supported by the visitation system 145, where such visitation sessions may include voice visitations, video sessions, email, online chats and/or text messaging services. In certain scenarios, the visitation session capabilities may allow a resident to participate in counseling sessions and diagnostic screening sessions. In certain scenarios, a portable communications device 110c may be referred to as an Intelligent Resident Device (IRD), or in a correctional institution environment, as an Intelligent Inmate Device (IID). In certain scenarios, a portable communications device 110c may be sponsored, or otherwise subsidized, by organizations or companies that have contracted with the controlled-environment facility to provide services to residents of the facility.

The portable communications device 110c may be especially adapted in various manners for use in a controlled-environment facility. For instance, in a correctional facility, the portability of a portable communications device 110c may be limited by mounting or otherwise attaching the device on a wall, within a booth or as part of a kiosk. As described in additional detail with regard to the embodiment of FIG. 2, the portable communications device 110c may include various adaptations that prevent unauthorized use of the device by residents. Such adaptations may include various restrictions on the resident's use of services provided by the resident communications system 100. The portable communications device 110c may be assigned for use by a resident on a temporary or permanent basis.

A portable communications device 110c may be restricted with respect to the network connectivity that is provided by the resident communications system 100. In many scenarios, a portable communications device 110c may be configured to connect only to a specific wireless access point 115, or a specific network of wireless access points, provided by the resident communications system 100. In certain embodiments, a portable communications device 110c may be further restricted to connect only to networks available within certain areas of a controlled-environment facility, such as a dedicated visitation area or other supervised area. In certain scenarios, network connectivity for a portable communications device 110c may be limited by placing wireless access points 115 and positioning directional antenna within the physical structure of a controlled-environment facility such that the generated wireless signals are restricted to limited areas within the facility.

In certain embodiments, resident communications device 110a-c may be a resident terminal 110a. As with the portable communications device 110c, the resident terminal 110a may provide residents of a controlled-environment facility with voice, video and/or text communications services. In certain scenarios, the resident terminal 110a may be mounted on a wall, within a booth, or as part of kiosk. In certain scenarios, the resident terminal 110a may be a hardened terminal and may be installed in an area of the controlled-environment facility 110 dedicated to providing residents with visitation sessions. In certain embodiments, resident terminal 110a may include a character-entry interface that allows data entry by residents and also allows residents to participate in text messaging or other text-based communication services. In certain embodiments, such a resident terminal 110a may be referred to as an Intelligent Facility Device (IFD).

In various embodiments, a resident terminal 110a may include a video display, a camera, and a handset that includes a microphone and speakers. The display may be any suitable electronic display such as, for example, a Liquid Crystal Display (LCD) or a touchscreen display (e.g., resistive, capacitive, etc.). The camera included on the resident terminal 110a may be any suitable imaging device such as, a video camera or webcam equipped with Charge-Coupled Devices (CCDs) or Complementary Metal-Oxide-Semiconductor (CMOS) active pixel sensors. A handset may be similar to a traditional telephone handset, including an earpiece portion (with a speaker), a handle portion, and a mouthpiece portion (with a microphone). In certain embodiments, the resident terminal 110a may allow a resident to utilize a headset with earphones and a microphone in place of a traditional handset.

As with the portable communications device 110c, the resident terminal 110a may provide residents with the ability to participate in visitation sessions supported by the visitation system 145, where such visitation sessions may include voice visitations, video sessions, email, online chats and/or text messaging services. In certain scenarios, the visitation session capabilities of the resident terminal 110a may allow a resident to participate in counseling sessions and diagnostic screening sessions, such as provided via screening module 135 and counseling module 170.

In certain embodiments, resident communications device 110a-c may be a resident kiosk 110b. As with the portable communications device 110c and the resident terminal 110a, the resident kiosk 110b may provide residents of a controlled-environment facility with voice, video and/or text communications services. In certain scenarios, the resident kiosk 110b may be located within a booth or other visitation area. The resident kiosk 110b may be formed from a hardened enclosure. In certain embodiments, resident kiosk 110b may include a keyboard or other character-entry interface that allows data entry and participation in text-based communication services.

As with the resident terminal 110a, a resident kiosk 110b may include a video display, a camera, a microphone and speakers that may provide residents with the ability to participate in visitation sessions supported by the visitation system 145, where such visitation sessions may include voice visitations, video sessions, email, online chats and/or text messaging services. The visitation session capabilities of the resident kiosk 110b may allow a resident to participate in counseling sessions and diagnostic screening sessions, such as provided via screening module 135 and counseling module 170.

As illustrated in FIG. 1, the resident terminal 110a and resident kiosk 110b may be coupled to the resident applications system 105 via one or more routers 175. In other embodiments, the resident terminal 110a and resident kiosk 110b may be coupled to the resident applications system 105 via one or more additional network devices in addition to router 175. In certain embodiments, each resident terminal 110a and resident kiosk 110b may be coupled to a router 175 via a network cable, where the router 175 and network cable are secured from being accessed by residents.

As illustrated, the resident applications system 105 includes an education module 120 and an entertainment module 125. These modules are software applications provided for use by residents and which may be utilized via a resident communications device 110a-c. The education module 120 may be one of many different modules provided for the education and training of residents. For instance, the education module 120 may provide a resident with access to recorded lectures, online classes, coursework materials, self-guided training courses, vocational training materials, job counseling services, job search services, and other such resources provided with the intent to rehabilitate and educate residents.

In addition to providing educational resources, the resident applications system 105 may include an entertainment module 125, by which entertainment software programs may be downloaded and run on a resident communications device 110a-c. In the illustrated embodiment, entertainment module 125 is comprised of a gaming module 130 and content module 135. The gaming module 130 may support the use of various games approved for residents of a controlled-environment facility. In certain scenarios, residents with particular privilege status classifications may be allowed access to certain games that are otherwise unavailable to other residents. The entertainment module 125 also includes a content module 135 that may be used to provide residents with various forms of content, such as recorded videos, live broadcasts, music files, access to streaming audio, and other audio and video content approved for residents of a controlled-environment facility. In certain embodiments, the content available to a particular resident may depend on a privilege status classification of the resident. For instance, residents having earned additional privileges may be allowed access to additional content via content module 135.

As described in additional detail with regard to the following embodiments, a resident's access to the software modules supported by the resident applications system 105 may be controlled based on the results of a mental health assessment of the resident. For instance, access to the games 130 and content 135 provided by the entertainment module 125 may be contingent on the resident submitting to a mental health assessment provided via screening module 165. The mental health screening may prevent a distressed resident from accessing games 130 and content 135 that could result in further agitation. In such scenarios, the screening module 135 may instead limit a distressed resident to accessing games 135 and content 130 that may instead serve to calm and redirect the resident. Access to visitation system 145 services may likewise be limited based on the results of a resident's mental health assessment. In certain embodiments, the screening module 135 may direct the resident to counseling services provided via a counseling module 170 of the resident application system 105 based on the results of a mental health assessment. In such scenarios, a resident directed to counseling may be prohibited from accessing certain modules and features of the resident applications system 105 until the resident has completed the required counseling.

In the embodiment of FIG. 1, the resident application system 105 is a component of the resident communications system 100. In certain embodiments, the resident application system 105 may be an external component of the resident communication system 100. In certain embodiments, one or more of the functions of the resident application system 105 may be provided by systems external to the resident communications system 100. In certain of such embodiments, one or more of the functions of the resident application system 105 may be provided by centralized systems external to the controlled-environment facility.

FIG. 2 is a block diagram of a communications device 200 configured according to certain embodiments for use by a resident of a controlled-environment facility. In various embodiments, the communications device 200 may correspond to a resident terminal 110a, a resident kiosk 110b, or a portable communications device 110c, such as described with respect to FIG. 1. In particular, the communications device 200 may be configured such that access to features of the device may be controlled based on screening of the resident. In particular, access to restricted features of the communications device 200 may be determined based on an assessment of the resident's current mental health status, where this assessment may be conducted based on inputs provided by the resident, and may additionally or alternatively be conducted using data collection capabilities of the communications device 200.

In certain scenarios, the communications device 200, such as resident terminal 110a, resident kiosk 110b and portable communications device 110c, allows residents to utilize various services provided by a resident communications system, such as described with respect to FIG. 1. The communications device 200 may be configured to interoperate with the resident communications system to utilize software applications that have been approved, and in some cases modified, for use by residents of a controlled-environment facility. Also as described with regard to FIG. 1, in certain embodiments, the resident communications system may be configured such that the resident may utilize the communications device 200 to participate in visitation sessions, including audio and/or video visitation sessions. In certain scenarios, these visitation session capabilities may allow the resident to participate in various counseling services with individuals that may be staff members of the controlled-environment facility and/or counselors participating from outside of the facility.

In various embodiments, the communications device 200 may be installed within a hardened enclosure that prevents any modifications to the hardware of the device and to prevent any tampering with the device that could allow a resident to conceal contraband within the device. In certain embodiments, the communications device 200 may be a tablet device, such as portable communications device 110c, that is protected within a hardened case that allows the resident to handle and use the portable device, but prevents the resident from accessing any of the device's internal components.

In certain embodiments, one or more sensors may be integrated into the communications device 200 in order to detect any such attempts to compromise the enclosure of the device. In certain embodiments, the communications device 200 may be configured to issue an alert to the resident communications system if the sensors indicate any attempts by a resident to compromise the enclosure of the device. In certain embodiments, the communications device 200 may be configured to shut down upon the sensors detecting an attempt to compromise the device, or in response to the sensors detecting sudden movements indicative of a resident's rough handling of the device. Various additional features of the hardware and/or software of the communications device 200 may be modified in order to prevent unauthorized use of the device.

Communications device 200 may include one or more processors 201. In various embodiments, the communications device 200 may be a single-processor system including one processor 201, or a multi-processor system including two or more processors 201. Processor(s) 201 may include any processor capable of executing program instructions, such as an Intel Pentium™ series processor or any general-purpose or embedded processors implementing any of a variety of Instruction Set Architectures (ISAs), such as the x86, POWERPC®, ARM®, SPARC®, or MIPS® ISAs, or any other suitable ISA.

Communications device 200 may include a chipset 202 that may include one or more integrated circuits that are connected to processor(s) 201. In certain embodiments, the chipset 202 may utilize a QPI (QuickPath Interconnect) bus 203 for communicating with the processor(s) 201. Chipset 202 provides the processor(s) 201 with access to a variety of resources. For instance, chipset 202 provides access to system memory 205 over memory bus 204. System memory 205 may be configured to store program instructions and/or data accessible by processors(s) 201. In various embodiments, system memory 205 may be implemented using any suitable memory technology, such as static RAM (SRAM), synchronous dynamic RAM (SDRAM), nonvolatile/Flash-type memory, or any other type of memory.

Chipset 202 may also provide access to a graphics processor 207. In certain embodiments, graphics processor 207 may be comprised within a video or graphics card that has been installed as components of the portable communications device 200. Graphics processor 207 may be coupled to the chipset 202 via a graphics bus 206 such as provided by an AGP (Accelerated Graphics Port) bus, a PCIe (Peripheral Component Interconnect Express) bus. The graphics processor 207 generates display signals that are provided to a display device 208, such as a tablet display screen. In certain embodiments, the display device 208 may be a touchscreen display configured to receive manual inputs, such as finger gestures and/or stylus inputs.

The chipset 202 of the communications device 200 may also include one or more hard disk and/or solid-state drives 215. As illustrated, the operating system 220 of the communications device 200 may be stored in the hard disk and/or solid-state drive 215. The communications device 200 may be configured to operate using a specially-adapted operating system 220, or operating system kernel, that implements various security procedures, such as the described authentication of the resident using a voice print, fingerprint or other biometric input recognition. The operating system 220 of the communications device 200 may also restrict the software applications and services that may be used by a resident. The operating system 220 may also be configured to prevent the resident from installing or modifying any applications on the device, thus limiting the resident to the use of software programs authorized for use by the resident communications system.

In certain embodiments, chipset 202 may be coupled to a network interface 209, such as provided by a Network Interface Controller (NIC). In certain embodiments, the network interface 209 may be coupled to the chipset 202 via a PCIe bus. As described, a communications device 200 such as portable communications device 110c, may be limited with regard to the network connectivity that is supported by the device. In such embodiments, the network interface 209 may be configured to restrict the wireless networks to which a portable communications device may be connected. For instance, network interface 209 may be a wireless network adapter that is configured to allow the communications device 200 to connect only to a specific wireless network provided by the resident communications system. In certain embodiments, network interface 209 may be configured to issue and alert notifying the resident communications system if any unrecognized wireless networks are detected by the communications device 200.

In many scenarios, use of a communications device 200 may be limited based on security protocols implemented by the resident communications systems. For instance, the operating system 220 of the communications device 200 may be configured to require a resident to enter a PIN (Personal Identification Number) assigned to the resident before enabling use of the communications device 200 by the resident. In other embodiments, the communications device 200 may likewise remain disabled until a resident trying to use the device is authenticated via a biometric verification. In certain embodiments, the communications device 200 may be configured to disable certain functions of the device or of the resident software applications installed on the device until the resident is authenticated, such as using voice print recognition of a voice sample provided by the resident in response to a prompt generated by the operating system 220. In the illustrated embodiment, the chipset 202 is configured to utilize I/O ports 210 that support biometric input devices 230, such as a fingerprint reader or a retinal scanner. In certain embodiments, the operating system 220 may boot upon initialization of the communications device 200, but may require authentication of the resident via biometric inputs 230 in order to enable the resident's use of the communications device 200.

In certain embodiments, a communication device 200, such as the resident terminal 110a or a kiosk 110b, may include an I/O port 210 input coupled to an RFID (Radio Frequency Identification) reader that is configured to detect RFID transponders worn by residents of the controlled-environment facility. The incorporation of the RFID reader into the communication device 200 provides the ability to authenticate an inmate using the communications device 200. In certain embodiments, the RFID reader may be configured receive reports of biometric information collected from sensors included in the RFID transponder device worn by a resident.

The I/O ports 210 of the communication device 200 may support various input devices that may be utilized as part of a mental health screening of a resident. For instance, a communication device 200, such as portable communications device 110c, may include a gyroscope coupled to the communications device 200 via an I/O port 210. Inputs from the gyroscope may be utilized by the screening module 225e in order to detect rough handling of the communications device 200, thus indicating a distress in the resident using the communications device 200. Additional inputs received via the I/O ports 210 of the communications device 200 may include audio captured using a microphone. Captured audio may be utilized by the screening module 225e in order to detect high levels of distress in the resident utilizing the communications device 200.

Other inputs received via the I/O ports 210 may receive collected biometric information such as heart rate and/or blood pressure readings. In certain embodiments, communications device 200 may include sensors, such as capacitive blood pressure and heart rate sensors, that collect biometric information indicative of a level of distress in the resident using the device. As described with regard to resident terminal 110a and resident kiosk 110b, in certain embodiments, communication device 200 may include an RFID reader capable of interfacing with an RFID chip included within a monitoring and tracking device worn by residents, where the monitoring and tracking device include sensors capable of measuring the resident's blood pressure and heart rate information.

In certain embodiments, the communication device 200 may be configured to periodically query available sensors in order to generate a baseline for the various biometric readings that may be collected using the sensors. For instance, communication device 200 may be configured to periodically query a resident's heart rate sensor in order to determine a baseline heart rate for that resident. The communication device 200 may be configured to transmit such periodically collected data to the screening module 165 for determination of baseline values for each biometric indicator for which readings have been collected from a resident. In certain embodiments, the screening module 165 may store baseline values determined for each resident in the resident account system 140, from which that may be retrieved in order to identify distresses residents by evaluating collected readings against base line values.

As described with respect to FIG. 1, the resident communications system may support the use of resident applications, such as the education module, the counseling module, the screening module and entertainment module, which may be downloaded and run on the communications device 200. Referring to FIG. 2, upon booting of the communications device 200, and upon instantiation and execution of the operating system instructions 220 stored in the storage drive 215, the operating system 220 provides the resident with access to various software modules 225*a-f*. Each of the software modules 225*a-f* may be installed on the communications device 200, but may remain fully or partially disabled until the resident has been approved to use the restricted software elements via a screening process implemented using a screening module 225*e*. In such embodiments, certain of the modules 225*a-f* and/or certain features of the modules 225*a-f* may be designated as restricted elements of the provided software, thus requiring screening of a resident before granting the resident with access to these restricted elements. In scenarios where the screening module 225*e* has detected distress in a resident, the resident may be prevented from utilizing restricted software elements until the resident has completed counseling provided using counseling module 225*f* or has otherwise been manually approved by a staff person.

The software modules supported by operating system 220 may include an education module 225*b* that provides residents with access to various educational services and resources. These educational services and resources provided via the education module 225*b* may include various forms of instructional materials, course materials, self-guided learning exercises, access to online classes, training materials, and/or vocational training exercises. In various embodiments, the services provided via the education module 225*b* may provide residents with various types of resources that promote the education of the resident. In certain embodiments, certain software modules, such as the education module 225*b*, may include restricted features. For instance, the features of the education module 225*b* that allow a resident to interact in live interactions with non-residents, such as live distance-learning lectures, may be designated as restricted features that require the resident to be screened prior to use, while other education module features, such as recorded educational content, may be non-restricted features that do not require screening. In certain scenarios, residents may be directed to such non-restricted features based on a screening outcome that indicates that the resident is distressed such that the resident should be limited to supervised interactions with non-residents.

The software modules supported by operating system 220 may also include a visitation module 225*a* that provides the allow the resident to participate in visitation sessions, such as the visitation sessions described with respect to FIG. 1. In certain embodiments, the visitation module 225*a* may provide residents with ability to request, schedule and participate in live visitation sessions, such as voice calls and video conferences. In such embodiments, the visitation module 225*a* may include user interface elements that allow the resident to interface with the visitation system 145 and the resident account system 140 in performing visitation functions such as requesting a visitation session, determining whether the requested visitation is allowed and scheduling a visitation session. The visitation module 225*a* may also include audio and video capabilities that allow the resident to participate in audio and video visitation sessions. Embodiments of the visitation module 225*a* may also enable residents to participate in other types of visitations, such as e-mail, text messaging and the exchange of voice and video messages. In certain embodiments, the visitation module 225*a* may be a restricted module, such that no features of the visitation module 225*a* remain disabled until the resident has been successfully screened.

The software modules supported by operating system 220 may also include an entertainment module 225*d* that may provide a resident with access to games and content, as described with respect to the entertainment services in FIG. 1. In certain embodiments, access to the entertainment module 225*d* may require a resident to submit to a mental health screening, which may be provided via the screening module 225*e*. In certain embodiments, certain games and/or content provided via the entertainment module 225*d* may be designated as restricted, thus requiring a resident to participate in a mental health assessment in order to access such content. In certain embodiments, certain games and/or content may be designated as non-restricted, with access to all other content requiring a mental health screening.

Once a resident using the communication device 200 has been properly authenticated, the resident may utilize features of the operating system 220 to request access to the supported software modules 225*a-f*. In certain embodiments, the operating system 220 may connect the resident to the resident applications system 105 of FIG. 1 in order to authorize a resident's use of a requested module or feature. In scenarios where a resident requests use of a restricted module or feature, such as access to entertainment module 225*d* or visitation module 225*a*, the operating system 220 may be configured to direct the resident to an assessment provided by screening module 225*e*. As described in additional detail with regard to the embodiment of FIG. 3, the results of the screening assessment taken by the resident may require the resident to undertake one or more counseling functions provided by the counseling module 225*f*.

In various embodiments, a communications device 200 does not include each of the components shown in FIG. 2. In various embodiments, communications device 200 may include various additional components in addition to those that are shown in FIG. 2. Furthermore, some components that are represented as separate components in FIG. 2 may in certain embodiments instead be integrated with other components. For example, in certain embodiments, all or a portion of the functionality provided by the illustrated components may instead be provided by components integrated into the one or more processor(s) 201 as a systems-on-a-chip.

FIG. 3 is a flowchart diagram illustrating certain steps of a process according to various embodiments, where the process begins at step 305 with the resident's use of a communications device 200 that includes a request to access a restricted software element. For instance, as described with respect to the above embodiments, a restricted software element may include a software module, such as a visitation module, or may include a feature of a software module, such as live, interactive educational courses, or may include content, such as games and videos that have been designated as restricted.

At step 310, the communications device 200 determines whether the requested software element is restricted. In certain scenarios, the communications device 200 may determine whether a software element is restricted based on data maintained locally on the communications device 200. In other scenarios, the communications device 200 may query the resident applications system 105 and/or the resident account system 140 in order to determine a restriction level for the requested software elements and whether the restriction level prohibits the requesting resident from accessing the requested software. In certain embodiments, a privilege status of a resident may allow that resident with limited access to restricted software elements without any requirement of a mental health assessment. In scenarios where the requested software is not restricted, at step 315, the resident may be granted use of the requested software element.

If the requested software element has been determined to be restricted, at step 320, the screening module of the communications device 200 may be enabled. As described, certain embodiments of the communications device 200 may limit a resident's access to the software modules installed on the device, included the screening module, unless the module is specifically enabled. Also as previously described, certain screening assessments may utilize sensor inputs supported by the communications device 200, such as a gyroscope that may be used to detect rough handling of the device or a biometric sensors providing blood pressure and heart rate information. In such scenarios, any such sensor inputs used for screening assessments may also be enabled. In certain embodiments, any enabled sensors may be queried to obtain current readings.

At step 325, the screening assessment to be administered may be determined. In certain embodiments, the selection of a screening assessment may be based on historical mental health assessment data maintained by the controlled-environment facility, such as in the resident account system 140. For instance, specific mental health assessments may be selected for a resident based on diagnosed conditions that have been associated with the resident in the resident account system 140. In some scenarios, a specific mental health assessment may be selected for a resident based on the results of a resident's mental health assessments that have been recently administered. In some scenarios, a mental health assessment may be selected based on the privilege status assigned to the resident by the controlled-environment facility. In some scenarios, a mental health assessment may be selected based on the specific software element that has been requested by the resident. For instance, a more stringent mental health assessment may be required to access certain video games provided via the entertainment module, while access to certain education resources may only require a brief mental health assessment.

The selected mental health assessment may be administered at step 330. The mental health assessment may require the resident to provide various types of inputs, such as key entry and verbal inputs. In certain embodiments, the inputs provided by the resident may be combined with biometric data collected using the sensor inputs supported by the communications device 200, such as the described use of a gyroscope to detect rough handling of the device and the use of sensors to collect heart rate and blood pressure information, that may be used to determine a resident's level of distress. Other sensor inputs may include capturing audio via the microphone of the portable device in order to evaluate the mental state of a resident, such as evaluating the characteristics of the resident's voice to determine whether the resident is distressed.

At step 335, the screening assessment may be graded to determine whether the resident is distressed or otherwise exhibiting signs of stress that indicate that the resident should not be allowed access to restricted software resources. In certain embodiments, an assessment may be graded based on an absolute scale for grading the administered assessment. In other embodiments, an assessment may be graded based on comparisons to baseline mental health information and/or previous test results for the resident. For instance, in the embodiment of FIG. 1, screening module 165 may retrieve baseline readings for a particular resident, which may then be compared against current readings in order to determine the resident's level of distress based on deviations from a baseline indicator levels for the resident.

In certain embodiments, the assessment may be graded strictly via a computer-implemented process, while other embodiments may utilize counselors or facility staff members to provide at least a portion of the assessment grading. At step 345, the grading of the administered assessment is used to determine whether the resident is distressed or otherwise under stress such that access to restricted software should be denied. In certain embodiments, the grading of the assessment may utilize a threshold value in evaluating a resident's biometric readings against baseline readings for the resident. In certain of such embodiments, the threshold value may be determined based at least in part by a privilege status associated with a resident. For instance, a high threshold value may be selected for a low-risk resident, thus allowing the resident greater leeway in using requested software elements, even when a certain level of distress is indicated based on comparisons of the resident's baseline biometric readings against current biometric readings. Conversely, a small threshold value may be selected for a high-risk resident, thus restricting such residents to using restricted software elements only when determined to be in a non-distressed state, as indicated by biometric readings that are relatively close to the resident's baseline readings.

In the illustrated embodiment, if a resident is determined to be in a distressed mental condition that warrants denying access to the requested software element, at step 350, the screening module determines whether the resident is required to participate in a counseling session. In certain scenarios, counseling may be required based on a resident's historical medical and mental health screening data that is maintained by the facility. In other scenarios, counseling may be required based on the scoring of the resident's assessment. At step 355, the required counseling is conducted. As described, required counseling may include use of the visitation capabilities of the resident's communication device in order for the resident to participate in a live, interactive counseling session. Other counseling may consist of self-guided exercises or directing the resident to the use of non-restricted software modules intended to calm the resident, such as educational or entertainment resources provided via the resident's communication device.

In certain scenarios, a heightened level of distress may be indicated in a resident, but live counseling may be unavailable at that time. In such scenarios, certain embodiments may generate an alert indicating the need for manual verification of the resident's condition, but nonetheless provide the resident with access to the restricted software element that has been requested by the resident. Such override procedures may be available to certain residents based on the privilege status of the resident. For instance, certain embodiments may recommend granting overrides to low risk residents, with these overrides logged and included in reports, but not requiring manual verification. High risk inmates may be allowed a limited number of over rides before manual verification of the resident's condition is required.

Certain embodiments may also provide the ability to configure notifications and alerts to be issued based on the detection of distressed residents. For instance, staff may configure alerts to be issued any time a resident seeking access to a restricted software element has been denied access multiple times due to detected distress. In another example, alerts may be configured based on the detection of a level of distress in a resident that surpasses an upper threshold that indicates potential danger to the resident or those that come in contact with the resident. In certain of such embodiments, an upper threshold may be selected for an individual resident based on baseline readings that have been collected for that resident. In other embodiments, a single upper threshold may be applied to all residents. Certain embodiments may provide staff with the ability to generate various reports providing information describing access to restricted software elements that has been denied or granted and the distress levels associated with those determinations. Such reports may be generated for access determinations made with respect to individual residents and/or for specific restricted software elements.

The foregoing has outlined rather broadly the features and technical advantages of the present invention in order that the detailed description of the invention that follows may be better understood. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

What is claimed is:

1. A communications device for providing services to a resident of a controlled-environment facility, the device comprising:
    a network interface configured to establish a connection with a resident communications system via one or more network access points located within the controlled-environment facility, wherein the network interface restricts the resident's network access using the communication device to the one or more network access points
    an RFID (Radio Frequency Identification) interface configured to receive biometric sensor information from an RFID transponder worn by the resident;
    a memory device configured to store operating system program instructions; and
    one or more processors configured to execute the operating system program instructions, causing the communications device to:
        connect with the resident communications system to provide the resident with use of a first software element;
        determine whether the first software element is a restricted software element of the communications device;
        if the first software element is determined to be a restricted software element, require the resident to complete a mental health assessment;
        administer the mental health assessment of the resident to determine a distress level of the resident, wherein the distress level is determined at least in part based on the biometric sensor information received from the RFID transponder worn by the resident, and wherein the mental health assessment further determines the distress level of the resident based on sensor inputs collected by the communications device that indicate rough handling of the communication device by the resident;
        allow the resident to utilize the first software element if the mental health assessment of the resident indicates the distress level of the resident is below a threshold; and
        provide the resident with use of a second software element if the mental health assessment of the resident indicates the distress level of the resident is above the threshold.

2. The communications device of claim 1, wherein the first software element comprises a software module providing the resident with one or more services.

3. The communications device of claim 1, wherein the first software element comprises a feature of a software module providing the resident with one or more services.

4. The communications device of claim 1, wherein the biometric sensor information received from the RFID transponder worn by the resident comprises at least one of a capacitive blood pressure sensor data and heart rate sensor data.

5. The communications device of claim 1, wherein the operating system program instructions further causing the communications device to:
    require the resident to complete a counseling session, if the mental health assessment of the resident indicates that the resident is distressed; and
    allow the resident to utilize the first software element, if the resident has completed the counseling session.

6. A system for providing a resident of a controlled-environment facility with communication services, the system comprising:
    one or more network access points coupled to a resident communications system;
    a communications device assigned to the resident, wherein the communications device is configured to connect to the resident communications system via the one or more network access points, and wherein the communication device restricts the resident's network access to the one or more network access points, and where the communication device comprises an RFID (Radio Frequency Identification) interface configured to receive biometric sensor information from an RFID transponder worn by the resident; and
    the resident communications system is configured to:
        receive a request from the resident for use of a first software element installed on the communications device;
        determine whether the first software element is a restricted software element of the communications device;
        if the first software element is determined to be a restricted software element, require the resident to complete a mental health assessment;
        administer the mental health assessment of the resident to determine a distress level of the resident, wherein the distress level is determined at least in part based on the biometric sensor information received from the RFID transponder worn by the resident, and wherein the mental health assessment further determines the distress level of the resident based on sensor inputs collected by the communications device that indicate rough handling of the communication device by the resident;
        allow the resident to utilize the first software element installed on the communication device, if the mental health assessment of the resident indicates the distress level of the resident is below a threshold; and provide the resident with use of a second software element installed on the communication device if the mental health assessment of the resident indicates the distress level of the resident is above the threshold.

7. The system of claim 6, wherein the first software element comprises a software module providing the resident with one or more services.

8. The system of claim 6, wherein the first software element comprises a feature of a software module providing the resident with one or more services.

9. The system of claim 6, wherein the biometric sensor information received from the RFID transponder worn by the resident comprises at least one of a capacitive blood pressure sensor data and heart rate sensor data.

10. The system of claim 6, wherein the resident communications system is configured to require the resident to complete a counseling session, if the mental health assessment of the resident indicates that the resident is distressed.

11. The system of claim 10, wherein the resident communications system is configured to allow the resident to utilize the first software element, if the resident has completed the counseling session.

12. A method for providing a resident of a controlled-environment facility with communication services via a communications device utilized by the resident, the method comprising:

connecting the communications device with a network access point of a resident communications system of the controlled-environment facility to provide the resident with use of a first software element; wherein the network access point is one of a network of network access points maintained by the controlled-environment facility; and wherein the communication device restricts resident's network access to the one or more network of network access points;

receiving, via an RFID (Radio Frequency Identification) interface of the communication device, biometric sensor information from an RFID transponder worn by the resident;

determining whether the first software element is a restricted software element of the communications device;

if the first software element is determined to be a restricted software element, requiring the resident to complete a mental health assessment;

administering the mental health assessment of the resident to determine a distress level of the resident, wherein the distress level is determined at least in part based on the biometric sensor information received from the RFID transponder worn by the resident, and wherein the mental health assessment further determines the distress level of the resident based on sensor inputs collected by the communications device that indicate rough handling of the communication device by the resident;

allowing the resident to utilize the first software element, if the mental health assessment of the resident indicates the distress level of the resident is below a threshold; and providing the resident with use of a second software element if the mental health assessment of the resident indicates the distress level of the resident is above the threshold.

13. The method of claim 12, wherein the first software element comprises a software module providing the resident with one or more services.

14. The method of claim 12, wherein the first software element comprises a feature of a software module providing the resident with one or more services.

15. The method of claim 12, wherein the biometric sensor information received from the RFID transponder worn by the resident comprises at least one of a capacitive blood pressure sensor data and heart rate sensor data.

16. The method of claim 12, further comprising: requiring the resident to complete a counseling session, if the mental health assessment of the resident indicates that the resident is distressed.

17. The method of claim 16, further comprising: allowing the resident to utilize the first software element, if the resident has completed the counseling session.

* * * * *